(12) United States Patent
Salini

(10) Patent No.: US 6,194,401 B1
(45) Date of Patent: Feb. 27, 2001

(54) PHARMACEUTICAL COMPOSITIONS CONTAINING CYCLOSPORINE AND A CARRIER COMPRISING AT LEAST AN ESTER OF α-GLYCEROPHOSPHORIC ACID

(75) Inventor: Alberto Salini, Lugano (CH)

(73) Assignee: Flarer S.A., Lugano (CH)

( * ) Notice: Subject to any disclaimer, the term of this patent is extended or adjusted under 35 U.S.C. 154(b) by 0 days.

(21) Appl. No.: 09/194,002

(22) PCT Filed: May 20, 1997

(86) PCT No.: PCT/EP97/02553

§ 371 Date: Nov. 18, 1998

§ 102(e) Date: Nov. 18, 1998

(87) PCT Pub. No.: WO97/44053

PCT Pub. Date: Nov. 27, 1997

(30) Foreign Application Priority Data

May 20, 1996 (IT) ............................................. MI96A1010

(51) Int. Cl.[7] ........................ A61K 31/33; A61K 31/685

(52) U.S. Cl. ............................ 514/183; 514/78; 514/825; 514/863; 514/895

(58) Field of Search ................... 514/183, 78, 825, 514/863, 895

(56) References Cited

U.S. PATENT DOCUMENTS

| 4,576,930 | | 3/1986 | Sugiyama et al. | 514/23 |
| 4,761,407 | | 8/1988 | Campan et al. | 514/179 |
| 5,342,625 | * | 8/1994 | Hauer et al. | 424/455 |
| 5,547,946 | | 8/1996 | Molinari | 514/129 |

FOREIGN PATENT DOCUMENTS

0697214 * 2/1996 (EP) .

* cited by examiner

Primary Examiner—Kevin E. Weddington

(57) ABSTRACT

A description is given of new pharmaceutical compositions containing cyclosporine, combined with a carrier comprising at least a derivative of α-glycerophosphoric acid, such as α-glycerophosphorylcholine, α-glycerophosphorylserine, α-glycerophosphorylethanolamine and α-glycerophosphoryl-myo-inositol, which allow cyclosporine bioavailability to significantly increase.

28 Claims, No Drawings

PHARMACEUTICAL COMPOSITIONS CONTAINING CYCLOSPORINE AND A CARRIER COMPRISING AT LEAST AN ESTER OF α-GLYCEROPHOSPHORIC ACID

The present application is the national stage filing of and claims priority to International Application No. PCT/EP97/02553, filed Mar. 20, 1997 and Italian Application Serial No. MI96A001010.

FIELD OF THE INVENTION

The following description sets forth new pharmaceutical compositions containing cyclosporine as active ingredient, combined with a carrier comprising an ester of α-glycerophosphoric acid, esterified on the phosphoric group with a choline, serine, ethanolamine or inositol hydroxyl group, which allow cyclosporine bioavailability to be significantly increased.

The claimed compositions are useful for the curative and symptomatic treatment of human and animal diseases wherefor cyclosporine is efficacious, e.g. inflammatory—especially chronic—states, rejection of transplanted organs or bone marrow, autoimmune diseases, tumours immunotherapy, parasitosis.

Cyclosporines are compounds having a peptide-cyclic chemical structure. Among cyclosporines, cyclosporin A is not only therapeutically important, but also commercially significant due to its high cost.

From a therapeutic point of view, cyclosporin A has decisively contributed to the success of organs and bone marrow transplantations, by effectively fighting the so-called "rejection phase", and proved to be particularly useful also for the treatment of autoimmune diseases, of some types of tumours and, in general, whenever a modulation of the immune system is required.

Lipid derivatives of glycerophosphorylcholine, glycerophosphoryl-ethanolamine, glycerophosphorylserine and glycerophosphoryl-inositol are widely distributed in nature combined in lecithins, cephalins, plasmalogens and phosphatidylserine (Remington's Sciences, Mack Publishing Ed., 18th Ed., 1990, p. 390).

L-α-glycerophosphorylcholine, herein referred to as GPC and commonly known as choline "alfoscerate" is produced on a commercial scale by biochemical processes, generally starting from lecithin and especially from soybean lecithin, and is absolutely biocompatible and non-toxic. GPC is highly soluble in water, has a sweet and agreeable taste, and is commercially available in the anhydrous form as a highly hygroscopic powder, although it is preferably marketed in the monohydrate form as a stable syrupy liquid.

TECHNICAL PROBLEM

Treatment with cyclosporine is seriously limited by the markedly low bioavailability of the drug, especially when orally administered. For example, cyclosporine administered within a soft gelatin capsule is slowly and not completely absorbed, showing bioavailability ranges from 20% to 50% of the dose administered (Goodman & Gilman's, "The Pharmacological Basis of Therapeutics", 9th Ed., p. 1299).

STATE OF THE ART

Several formulations have been investigated with a view to solving the problem of cyclosporine low availability. To this end, several compounds, either alone or as a mixture thereof, were used as carriers of the drug to improve its absorbability and bioavailability. For example, U.S. Pat. No. 5,342,625 describes compositions in the form of preconcentrated water-dispersible microemulsions, including cyclosporine, a lipophilic phase consisting of triglycerides of fatty acids, a hydrophilic phase consisting of polethylene glycol ethers, and surfactants, e.g. phospholipids (lecithins). However, the problem of cyclosporine bioavailability has never been satisfactorily solved, and also the treatment cost-benefits ratio is not satisfactory.

Furthermore, the various carriers cause several problems connected with their therapeutic use. For example, most compounds obtained by chemical synthesis are absolutely non-physiological or are not entirely physiological; others, exhibiting a non-negligible toxicity, may also increase the toxicity index of cyclosporine; some may contain even highly toxic impurities derived from the process of synthesis, or originate negative secondary reactions when metabolized (e.g. glycerides with fatty acids, transesterified oils, vegetable oils may undergo lipoperoxidation with consequent formation of "free radicals", which are extremely noxious to cellular structures); some may easily cause gastric and intestinal intolerance and seriously irritate the mucous membranes and/or vascular walls (as is the case, e.g., of some carriers having surface-active, emulsifying surface-active, dispersing, solubilizing properties, etc.).

SUMMARY

The Applicant has now surprisingly found that by combining cyclosporine with a carrier including α-glycerophosphorylcholine or other esters of α-glycerophosphoric acid, e.g. α-glycerophosphorylethanolamine, α-glycerophosphorylserine, or α-glycerophosphorylinositol, cyclosporine bioavailability is considerably improved.

It is, therefore, an object of the present invention to provide pharmaceutical compositions containing cyclosporine as active ingredient in a therapeutically effective dose, characterized in that they comprise a cyclosporine and at least an ester of α-glycerophosphoric acid selected from the group consisting of α-glycerophosphorylcholine, α-glycerophosphorylethanolamine, α-glycerophosphorylserine, α-glycerophosphorylinositol, and salts or pharmaceutically acceptable complexes thereof.

In addition to the aforesaid carriers, the compositions of the present invention may optionally contain additional components, such as pharmaceutically acceptable excipients and/or diluents other than the aforesaid esters of α-glycerophosphoric acid with choline, ethanolamine, serine or inositol.

It is a further object of the present invention to use the claimed formulations to treat the diseases for which cyclosporines are used.

DETAILED DESCRIPTION OF THE INVENTION

In the claimed compositions, the cyclosporine is preferably cyclosporin A.

As used herein, the expression "esters of α-glycerophosphoric acid" means all possible isomers, i.e. both the optically active and the racemic forms.

With the objects of the present invention in view, it is therefore possible to use the esters of α-glycerophosphoric acid (also known as α-glycerylphosphoric- or glycero-3- phosphoric acid), the stereoisomers in which the configuration of the asymmetric carbon atom in position 2 of the glyceric residue is L or D, or mixtures thereof; furthermore, in glycerophosphorylserine, the serine-derived residue may be L or D or mixtures thereof, and in glycerophosphorylinositol the inositol residue derives from any of its isomers and mixtures thereof.

The compounds useful for the preparation of the claimed compositions correspond to the derivatives of formula (I)

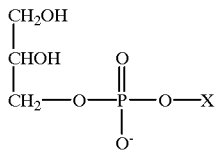
(I)

where X is selected from the group consisting of
a)

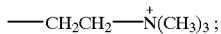

b)

c) —CH$_2$CH(NH$_2$)COOH d) residue R—, deriving from ROH, where ROH is an inositol, and salts or pharmaceutically acceptable complexes thereof.

The inositol is typically myo-inositol.

The salts may be, e.g., the salts with alkali metals or alkaline-earth metals, e.g. sodium, potassium or calcium salts of the compound of formula (I), where X is as defined under c) [α-glycerophosphorylserine], or of compounds of formula (I) where X is as defined under d) [α-glycerophosphorylinositol], for instance α-glycerophosphorylinositol calcium salts.

It is also possible to use α-glycerylinositol derivatives in which one or more hydroxyl groups of the inositol residue are esterified with phosphate groups.

The esters of α-glycerophosphoric acid, which may be conveniently used as cyclosporine carriers in the claimed compositions, are characterized by the presence of two hydroxyl groups of the glyceric residue in the free form and, therefore, differ considerably in their chemical structure and physicochemical properties from the corresponding derivatives in which one or both of the aforesaid hydroxyl groups are esterified with fatty acids residues (i.e. acids combined in lipids), such as it occurs in natural or synthetic phospholipids (e.g. lecithins).

Surprisingly, α-glycerylphosphorylcholine and the other esters of α-glycerylphosphoric acid, selected as cyclosporine carriers for the purposes of the present invention, proved to be able increase cyclosporine bioavailability. This is especially surprising in consideration of the fact that the compositions of the prior art, like the aforementioned ones, intended to obtain a good cyclosporine bioavailability, contain lipidic materials, e.g. phospholipids, as surfactants.

According to particular embodiments of the present invention, the compositions containing cyclosporine are substantially free from lecithins and generally from phosphatides (phospholipids) and/or lysophospholipids corresponding to the compounds selected as carriers (such as cephalins, plasmalogens and phosphatidylserines) and more generally even from glycerylphosphoric acid derivatives, in which one or both of said hydroxyl residues are acylated with fatty acids residues.

More generally, particular embodiments of the present invention may be free from glyceryl esters of fatty acids, e.g. fats and oils. It follows that they do not cause the inconveniences brought about by the aforementioned formulations containing lecithins or lipidic materials known in the art.

Preferably, the esters of α-glycerylphosphoric acid useful for the preparation of the compositions according to the present invention are esters of L-α-glycerophosphoric acid, selected from the group consisting of L-α-glycerophosphorylcholine (GPC), L-α-glycerophosphorylethanolamine (GPE), L-α-glycerophosphorylserine (GPS) and L-α-glycerophosphoryl-D-myo-inositol (GPmI).

Typically, GPC and GPE are used as are, i.e. as inner salts, not salified with other ions.

GPmI may be, e.g., used as a calcium salt [(GPmI)$_2$Ca]. α-Glycerophosphorylserine may be, e.g. in the form of an alkali metal salt (sodium or potassium).

Several esters of α-glycerophosphoric acid useful as carriers in the compositions of the present invention, such as L-α-glycerylphosphorylcholine (GPC) and L-α-glycerylphorphorylethanolamine (GPE) (inner salts), and L-α-glycerylphosphoryl-D-myo-inositol calcium salt (GPmI)$_2$Ca, are available from Prime European Therapeutical S.p.A. (Euticals S.p.A.), or may be prepared by known methods, for instance as described in U.S. Pat. No. 5,250,719.

According to a typical embodiment of the present invention, L-α-glycerophosphorylcholine (GPC) (inner salt), also known as choline "alfoscerate", is used as a carrier.

L-α-glycerylphosphorylcholine (GCP) may be used in the anhydrous form or as a monohydrate, depending on the type of pharmaceutical form to be prepared. However, for reasons of stability and handiness, the monohydrate is generally preferred.

In the compositions of the present invention, the total concentration of the esters of α-glycerophosphoric acid as well as the ratio by weight of cyclosporine to the aforesaid esters may vary within a wide range and depend, e.g., on the consistency of the admixture to be prepared, on the specific α-glycerophosphoric acid derivative used and, in particular, on their solvent action, on the cyclosporine concentration in the final composition, and on the solvent action of the other pharmaceutical excipients, if any.

Typically, in the formulations of the invention, the ratio by weight of cyclosporine to the ester of α-glycerophosphoric acid ranges from 1:0.1 to 1:50, preferably from 1:0.1 to 1:10, and more preferably from 1:0.5 to 1:5.

The pharmaceutical compositions according to the present invention are particularly suitable for oral or parenteral administration, more particularly for oral administration.

The compositions according to the present invention are prepared by conventional techniques, i.e. by admixing cyclosporine and the ester of α-glycerophosphoric acid, optionally with one or more excipients and/or diluents.

Preferably, cyclosporine is carefully premixed with the ester of α-glycerophosphoric acid. The resulting admixture is added with excipients, if any, and diluted with an appropriate solvent if liquid formulation are to be obtained. The admixtures so obtained, which are solid (powders), semisolid or liquid, depending on the type and amount of α-glycerophosphoric acid used and on the type and amount of the other excipients, if any, may be administered as are or incorporated in solid or semisolid pharmaceutical formulations obtained by conventional techniques, such as packets, hard or soft capsules, tablets, pills, or as liquid or semiliquid formulations, such as solutions or suspensions to be administered per os or by injection, for example solutions to be administered in the form of drops, syrups, or in vials.

The excipients other than the aforesaid esters of α-glycerophosphoric acid useful herein are conventional excipients, e.g. silica to obtain powders, or other excipients for tablets, such as lubricants, e.g. magnesium stearate, binding and/or disintegrating agents, or other useful excipients, such as pharmaceutically acceptable flavouring and colouring agents. Examples of excipients are propylene glycol, polyethylene glycol and polyvinylpyrrolidone.

The diluents that may be used to prepare solutions or dispersions according to the present invention are, e.g., water, alcohols (e.g. ethanol, polyethylene glycols) and mixtures thereof.

The compositions of the present invention may of course be added with one or more active ingredients exerting a complementary therapeutic action, such as the glucocorticoids (cortisone, and derivatives and homologues thereof), cytotoxic drugs, specific antibodies, vitamins, etc.

Typical embodiments of the present invention contain cyclosporine admixed with the ester of α-glycerophosphoric acid, formulated in the form of
a) capsules for oral administration;
b) tablets for oral administration;
c) solutions for oral administration (e.g. drops) or for parenteral administration;
d) vials for parenteral administration, in which one or more solid components are separately contained in one or more vials to be mixed immediately prior to administration with a diluent in a further separate vial.

Solid admixtures in the form of powders including cyclosporine, the ester of glycerophosphoric acid and optionally one or more excipients, are for example obtained by careful admixture of cyclosporine with an ester of α-glycerophosphoric acid, both in the solid form, e.g. cyclosporin A and anhydrous L-α-glycerylphosphorylcholine (GPC), and optionally with one or more solid excipients, e.g. silica or magnesium stearate.

Solid, semisolid or liquid admixtures are, e.g., prepared by kneading a cyclosporine (powder) with an ester of liquid α-glycerophosphoric acid, and optionally with an excipient. The admixtures consistency, from solid to semisolid or liquid, depends on the ratio by weight of cyclosporine to the ester of α-glycerophosphoric acid and on the type and amount of excipients and/or diluents used.

For example, cyclosporin A and L-α-glycerylphosphorylcholine (GPC) monohydrate are carefully kneaded and the formulations obtained are solid or semisolid or liquid depending on the GPC/cyclosporine ratio used.

Semisolid or liquid admixtures are, e.g., obtained by dispersing or dissolving a solid cyclosporine and a liquid or solid ester of α-glycerophosphoric acid, e.g. cyclosporin A and L-α-glycerylphosphorylcholine (GPC), in the anydrous form or as a monohydrate, preferably added with an excipient, e.g. a dispersing agent(e.g. a surfactant) such as polyethylene glycol 200, in an appropriate liquid diluent, e.g. a solvent such as ethanol (e.g. ethanol 95°).

Preferably, cyclosporine is premixed with the ester of α-glycerophosphoric acid, optionally in the presence of the dispersing agent, and diluted with a suitable diluent or solvent.

The solid, semisolid or liquid formulations obtained may be used as are or may be further formulated as appropriate.

For example, solid admixtures may be enclosed in a hard gelatin matrix while semisolid or liquid admixtures may be coated with a soft gelatin layer, to give hard and soft capsules, respectively.

The solid, semisolid or liquid admixtures useful to fill the capsules contain cyclosporine and the ester of α-glycerophosphoric acid in a ratio by weight ranging, for instance, from 1:0.5 to 1:5; the solid or semisolid admixtures may contain, e.g., 20% to 70% by weight of cyclosporine, 30% to 80% by weight of α-glycerophosphoric acid derivative and the liquid admixtures may contain e.g. 20% to 40% by weight of cyclosporine, 20% to 40% by weight of the ester of α-glycerophosphoric acid and optionally 10% to 20% by weight one or more excipients, in a diluent such as ethanol (e.g. ethanol 95°) (by weight % amounts are referred to the total weight of the admixture used as capsule filling).

Compressed tablets may be, e.g., obtained by careful admixture of cyclosporine with the ester of α-glycerophosphoric acid, preferably cyclosporin A and anhydrous L-α-glycerylphosphorylcholine (GPC), and with one or more appropriate excipients, such as lubricants, binding or disintegrating agents, each being in the solid state. The resulting powdery admixture is generally passed through adequate porosity sieves and subjected to compression.

Exemplary tablets of the present invention contain cyclosporin A, anhydrous L-α-glycerylphosphorylcholine (GPC) and magnesium stearate as a lubricant.

Typical examples of powdery admixtures for tablets contain cyclosporine and carriers in weight ratios ranging from 1:0.5 to 1:5; furthermore, they contain, e.g., about 20% to 40% by weight of cyclosporine, 20% to 40% by weight of the ester of solid α-glycerophosphoric acid (typically an ester of L-α-glycerophosphoric acid), and 50% to 70% by weight of a lubricant.

For instance, according to some exemplary embodiments of the present invention, a cyclosporine and at least one of said ester of α-glycerophosphoric acid are added with a hydrophilic vehicle (e.g. water, ethanol or mixtures thereof), for instance in the presence of a surfactant (e.g. hydrophilic surfactant).

A further exemplary embodiment of the present formulations is a solution to be administered as drops, comprising cyclosporine, typically cyclosporin A, and an ester of α-glycerophosphoric acid, e.g. L-α-glycerophosphorylcholine (GPC) monohydrate, dissolved in an appropriate solvent, such as ethanol (e.g. ethanol 95°), preferably in the presence of a surfactant, e.g. a hydrophilic non-ionic surfactant, such as polyethylene glycol 200.

Said preparation may, e.g., contain cyclosporine and an ester of α-glycerophosphoric acid in ratios by weight ranging from 1:0.5 to 1:5, and contain, e.g., about 5% to 20% by weight of cyclosporine, about 20% to 50% by weight of an ester of α-glycerophosphoric acid, and about 30% to 60% by weight of a surfactant.

According to a further exemplary embodiment of the present invention, admixtures of cyclosporine with an ester of α-glycerophosphoric acid are formulated as preparations for injection in vials. For example, one vial contains cyclosporine, typically cyclosporin A, in the dry state, and another vial contains the ester of α-glycerophosphoric acid, typically L-α-glycerylphosphorylcholine (GPC) monohydrate, either dissolved or dispersed in a pharmaceutically acceptable diluent, e.g. sterile distilled water for injection, preferably containing a dispersing agent (e.g. an emulsifier), such as polyvinylpyrrolidone.

The composition in vials may, e.g., contain cyclosporine and the ester of α-glycerophosphoric acid in ratios ranging from 1:5 to 1:10 by weight, and contain, e.g., 1% to 5% by weight of cyclosporine, about 10% to 30% by weight of the ester of α-glycerophosphoric acid, and 1% to 10% by weight of dispersing agent.

The active ingredient dose that may be administered with the compositions of the present invention depend on the way of administration, on the effect to be produced and on the patient's state of health.

For instance, the unit dosage for compositions for human administration ranges from about 10 mg to about 200 mg cyclosporine for the oral administration route and from about 5 mg to 100 mg cyclosporine for the parenteral (injective) route, although different doses may also be administered: the aforementioned unit dosage forms may be administered to the subject treated one or more times a day, for instance from 1 up to 3–5 times daily (e.g. referred to a human subject with about 70 kg of body weight), the overall daily dose depending e.g. on the particular purpose of therapy, the phase of therapy, the patient's age etc. Just as an example, in human therapy, to obtain immunosuppression for the prevention and treatment of transplant rejection, cyclosporine can be orally administered at daily dosages of 5–15 mg/Kg of body weight per day for the initial treatment, and of 1–10 mg/Kg per day for the maintenance treatment, whereas for the treatment of rheumatoid arthritis, cyclosporine daily dosages by the oral route can be for instance of 1–5 mg/Kg of body weight per day, generally divided into two administrations.

The amount of esters of glycerophosphoric acid administered with the composition of the present invention ranges, e.g., from about 5 mg to about 200–300 mg per unit dose of composition for oral use, and from about 100 mg to about 1.5 g per unit dose of composition for parenteral use.

The claimed compositions are useful for the curative and symptomatic treatment of human and animal diseases wherefor cyclosporine is active, e.g. inflammatory—especially chronic—states, autoimmune inflammatory states, such as rheumatoid arthritis, other autoimmune diseases, such as psoriasis and endogenous uveitis; pathological states associated with the rejection of transplanted organs or bone marrow, tumours immunotherapy, diseases caused by parasites (such as malaria, coccidiomycosis, schistosomiasis).

Surprisingly, the formulations according to the present invention allow a markedly increase cyclosporine bioavailability to be achieved, which results in a significant increase in its therapeutic index, with the cost/benefits ratio being remarkably shifted in favour of benefits. At the same time, the aforementioned disadvantages of the carriers of the prior art are herein substantially absent or drastically reduced.

In particular, the claimed compositions provide several benefits: new types of toxic effects of cyclosporine are not observed; the gastric and intestinal tolerability is considerably improved; the irritative phenomena following the use of parenteral formulations, commonly occurring with the preparations already known and almost exclusively ascribable to the carriers used, are significantly reduced or substantially absent.

Also the palatability of the formulations for oral administration obtained according to the present invention is definitely superior to that of several preparations already known, such as those containing in particular carriers having an oily feel or bitter taste or a disagreeable aftertaste. As known, palatability can be a fundamental factor in the success of a therapeutic treatment, especially when drug administration over a long period of time is required.

Some embodiments of the present invention are reported below by way of example and not of limitation.

The formulations described below were obtained with cyclosporin A as an active ingredient and L-α-glycerylphosphorylcholine (GPC) inner salt [(R)-ethanimino,2-[(2,3-dihydroxypropoxy)hydroxy phosphonyl)oxy]N,N,N-trimethylhydroxide, inner salt], available from Eutical S.p.A.

EXAMPLE 1

| HARD CAPSULES | |
|---|---|
| Cyclosporin A | 1 g |
| GPC monohydrate | 0.5 g |

The above ingredients were carefully kneaded until obtaining a powder which was used to produce capsules, each containing 0.020 g to 0.200 g cyclosporine.

Cyclosporine/GPC weight ratio=1:05.

EXAMPLE 2

| SOFT CAPSULES | |
|---|---|
| Cyclosporin A | 1 g |
| GPC monohydrate | 5 g |

The above ingredients were carefully kneaded until obtaining a milk-white semifluid suspension which was used to produce soft gelatin capsules, each containing 0.020 g to 0.200 g cyclosporine.

Cyclosporine/GPC weight ratio=1:5.

EXAMPLE 3

| TABLETS | |
|---|---|
| Cyclosporin A | 1 g |
| Anhydrous GPC | 1 g |
| Magnesium stearate | 3 g |

The above ingredients were carefully admixed and the powder passed through a 40 mesh sieve screen. Tablets were produced, each containing 0.010 g to 0.100 g cyclosporine.

Cyclosporine/GPC weight ratio=1:1.

EXAMPLE 4

| SOFT CAPSULES | |
|---|---|
| Cyclosporin A | 1 g |
| GPC monohydrate | 0.8 g |
| Polyethylene glycol 200 | 0.500 g |
| Ethanol (95°) | 0.800 g |

The above ingredients were carefully admixed until obtaining a solution. Soft capsules were produced, each containing 0.010 g to 0.200 g each cyclosporine.

Cyclosporine/GPC weight ratio=1:08.

EXAMPLE 5

| SOLUTION TO BE ADMINISTERED AS DROPS | |
|---|---|
| Cyclosporin A | 1 g |
| GPC monohydrate | 4 g |
| Ethanol (95°) | 3 g |
| Polyethylene glycol 200 | 5 g |

The above ingredients were carefully admixed until obtaining a clear solution, made available, for oral administration, in bottles with dropper.

30 drops=1.3 g formulation=0.100 g cyclosporin.

With this formulation, the cyclosporine posology may be modulated according to the patient's requirements.

Cyclosporine/GPC weight ratio=1:4.

EXAMPLE 6

PARENTERAL PREPARATION IN VIALS

| a) | Cyclosporin A | 0.1 g |
|---|---|---|
| b) | GPC monohydrate | 1 g |
|  | Polyvinylpyrrolidone | 0.1 g |
|  | Sterile distilled water | 5 g |

Cyclosporine was metered to a bottle for injection use. Mixture b) was solubilized and metered to the vial containing the solvent.

Immediately prior to administration, solution a) was introduced into the bottle containing b) by the usual procedure. The suspension was shaken before using and injected.

Cyclosporine/GPC weight ratio=1:10.

What is claimed is:

1. A pharmaceutical composition containing a cyclosporine as active ingredient, characterized in that it comprises a cyclosporine and as a carrier at least an ester of α-glycerophosphoric acid selected from the group consisting of α-glycerophorylcholine, α-glycerophorylethanolamine, α-glycerophorylserine, α-glycerophorylinositol, salts and pharmaceutically acceptable complexes thereof.

2. The composition as claimed in claim 1, substantially free from lecithins, cephalins, plasmalogens and phosphatidylserines.

3. The composition as claimed in claim 1, wherein cyclosporine is cyclosporin A.

4. The composition as claimed in claim 1, wherein said ester of α-glycerophosphoric acid is an ester of L-α-glycerophosphoric acid selected from the group consisting of L-α-glycerophosphorylcholine (GPC), L-α-glycerophorphorylethanolamine (GPE), L-α-glycerophosphorylserine (GPS) and L-α-glycerophosphoryl-D-myo-inositol (GPmI).

5. The composition as claimed in claim 1, wherein said ester of the α-glycerophosphoric acid is L-α-glycerophosphorylcholine (GPC).

6. The composition as claimed in claim 5, wherein L-α-glycerophosphorylcholine (GPC) is in the monohydrate or anhydrous form.

7. The composition as claimed in claim 1, wherein the ratio by weight of cyclosporin to the ester of the α-glycerophosphoric acid ranges from 1:0.1 to 1:50.

8. The composition as claimed in claim 7, wherein said ratio ranges from 1:0.1 to 1:10.

9. The composition as claimed in claim 8, wherein said ratio ranges from 1:0.5 to 1:5.

10. The composition as claimed in claim 1 suitable for oral or parenteral administration.

11. The composition as claimed in claim 1 suitable for oral administration.

12. The composition as claimed in claim 1 in the form of packets, hard or soft capsules, tablets, or pills.

13. The composition as claimed in claim 1 in the form of a solution or suspension to be administered orally or by injection.

14. The composition as claimed in claim 1, selected among:
  a) capsules for oral administration;
  b) tablets for oral administration;
  c) solutions for oral administration or for parenteral administration;
  d) vials for parenteral administration, in which one or more solid components are separately contained in one or more vials and mixed immediately prior to administration with a diluent in a separate vial.

15. The composition as claimed in claim 1 also containing at least an active ingredient exerting a complementary therapeutical action, selected from the group consisting of glucocorticoids, cytotoxic drugs, antibodies and vitamins.

16. The composition as claimed in claim 1 containing a unit dose of 10 mg to 200 mg cyclosporine for oral administration, and of 5 mg to 100 mg cyclosporine for parenteral administration.

17. The composition as claimed in claim 1 useful for the treatment of human and animal diseases.

18. The composition as claims in claim 1, useful in the treatment of inflammatory states, pathological states associated with the rejection of transplanted organs or bone marrow, autoimmune diseases, tumours immunotherapy, or diseases caused by parasites.

19. The composition as claimed in claim 18, wherein the inflammatory states are chronic inflammatory states or autoimmune inflammatory states; the autoimmune diseases are rheumatoid arthritis, psoriasis or endogenous uveitis; the diseases caused by parasites are malaria, coccidiomycosis, schistosomiasis.

20. Process for the preparation of a composition as claimed in claim 1, wherein cyclosporine is admixed with at least an ester of α-glycerophosphoric acid, optionally in the presence of one or more components selected out of excipients, diluents and mixtures thereof.

21. A process as claimed in claim 20, wherein cyclosporine and the ester of α-glycerophosphoric acid are carefully premixed, then optionally added with excipients, and optionally diluted with an appropriate diluent, if liquid formulations are to be obtained.

22. A process as claimed in claim 20, wherein cyclosporine is carefully admixed with an ester of α-glycerophosphoric acid, both in the solid states, and optionally with one ore more solid excipients, to give a solid admixture.

23. A process as claimed in claim 20, wherein cyclosporine (powder) is kneaded with a liquid ester of α-glycerophosphoric acid and optionally with an excipient to give solid, semisolid or liquid admixtures.

24. A process as claimed in claim 20, wherein cyclosporine and a liquid or solid ester of α-glycerophosphoric acid are dispersed or dissolved in the presence of a dispersing agent, in a liquid diluent, to give a semisolid or liquid admixture.

25. A process as claimed in claim 20, wherein said α-glycerophosphoric acid is L-α-glycerylphosphorylcholine.

26. Method of use of an ester of α-glycerophosphoric acid, said method comprising selecting and using said ester as a carrier for preparing and using pharmaceutical compositions containing cyclosporine as active ingredient as claimed in claim 1.

27. A composition obtainable according to claim 20.

28. A therapeutic method for the treatment of a disease selected from the group consisting of inflammatory states, pathological states associated with the rejection of transplant organs or bone marrow, autoimmune diseases, tumors, immunotherapy and diseases caused by parasites, which comprises administering to a subject in a need of such a treatment a therapeutically effective amount of a composition as claimed in claim 1.

* * * * *